United States Patent
Ostermaier

(10) Patent No.: US 7,208,632 B2
(45) Date of Patent: Apr. 24, 2007

(54) SEPARATION OF 6-AMINOCAPRONITRILE AND HEXAMETHYLENEDIAMINE FROM A MIXTURE COMPRISING HEXAMETHYLENEDIAMINE, 6-AMINOCAPRONITRILE AND TETRAHYDROAZEPINE

(75) Inventor: John Joseph Ostermaier, Orange, TX (US)

(73) Assignee: Invista North America S.A R.L., Wilmington, DE (US)

( * ) Notice: Subject to any disclaimer, the term of this patent is extended or adjusted under 35 U.S.C. 154(b) by 216 days.

(21) Appl. No.: 10/939,144

(22) Filed: Sep. 10, 2004

(65) Prior Publication Data

US 2006/0058555 A1    Mar. 16, 2006

(51) Int. Cl.
*C07C 209/86* (2006.01)
(52) U.S. Cl. .................. 564/498; 564/497; 558/435; 540/612
(58) Field of Classification Search .............. None
See application file for complete search history.

(56) References Cited

U.S. PATENT DOCUMENTS 6,139,693 A * 10/2000 Bassler et al. ............... 203/49
6,248,926 B1 * 6/2001 Ostermaier et al. ......... 564/492

* cited by examiner

*Primary Examiner*—Brian Davis

(57) ABSTRACT

The invention relates to the field of separation by distillation of 6-aminocapronitrile (ACN) and hexamethylenediamine (HMD) from a mixture comprising ACN, HMD, tetrahydroazepine (THA), adiponitrile (ADN) and low boilers (LB). Also disclosed is a method for producing a distillate stream comprising HMD; a side draw stream comprising ACN, THA and low levels of dimers of ACN and HMD; and a tails stream comprising ACN, THA and substantially higher levels of dimers of ACN and HMD than found in the side draw stream. The side draw stream is particularly suitable for use in the production of caprolactam since the low levels of dimers of ACN and HMD do not greatly affect the catalyst life in the caprolactam production process. The tails stream can be further distilled to produce a tails distillate stream comprising ACN and THA, which can be recycled back to the first distillation column, further increasing recovery of ACN from the feed stream. Process conditions of the method of the invention disfavor the production of 2-cyanocyclopentylideneimine (CPI).

12 Claims, 1 Drawing Sheet

Figure 1:
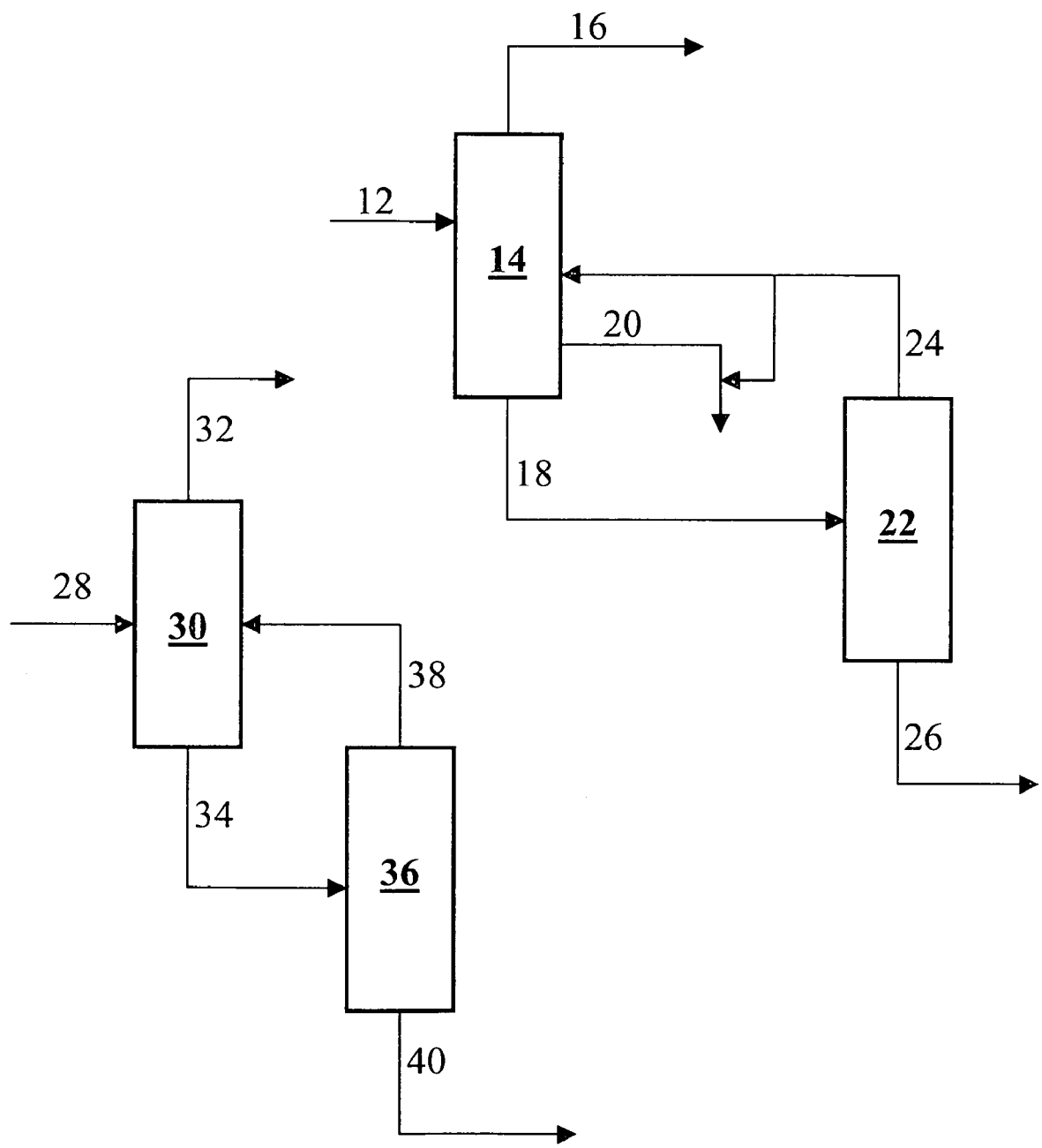

SEPARATION OF 6-AMINOCAPRONITRILE AND HEXAMETHYLENEDIAMINE FROM A MIXTURE COMPRISING HEXAMETHYLENEDIAMINE, 6-AMINOCAPRONITRILE AND TETRAHYDROAZEPINE

FIELD OF THE INVENTION

The invention relates to the field of separation by distillation of 6-aminocapronitrile (ACN) and hexamethylenediamine (HMD) from a mixture comprising ACN, HMD, tetrahydroazepine (THA), adiponitrile (ADN) and low boilers (LB). Also disclosed is a method for producing a distillate stream comprising HMD; a side draw stream comprising ACN, THA and low levels of dimers of ACN and HMD; and a tails stream comprising ACN, THA and substantially higher levels of dimers of ACN and HMD than found in the side draw stream. The side draw stream is particularly suitable for use in the production of caprolactam since the low levels of dimers of ACN and HMD do not greatly affect the catalyst life in the caprolactam production process. The tails stream can be further distilled to produce a distillate stream comprising ACN and THA, which can be recycled back to the first distillation column, further increasing recovery of ACN from the feed stream. Process conditions of the method of the invention disfavor the production of 2-cyanocyclopentylideneimine (CPI).

BACKGROUND OF THE INVENTION

It is well known in the Nylon industry that ADN can be hydrogenated catalytically to produce HMD by complete hydrogenation, or mixtures of ACN and HMD by partial hydrogenation. HMD can be used in the manufacture of Nylon 6, 6. The hydrogenation reaction product also contains unreacted ADN and unwanted byproducts such as THA. After hydrogenation, the reaction product must be refined, generally by methods involving fractional distillation, and HMD and ACN must be separated from each other.

It is also known that if the refining conditions involve too high a temperature, the unreacted ADN can isomerize into CPI. The CPI generally distills with the ADN, and can form AMCPA (2-aminomethylcyclopentylamine) if it is recycled back to the hydrogenation reactor. AMCPA, if unseparated from the HMD, can cause inferior Nylon 6, 6 to be made.

U.S. Pat. Nos. 6,346,641 and 6,462,220 teach distillation processes to separate ACN and HMD in which the column temperatures are kept below 185 degrees C. However, neither of these patents teach methods that allow distillation to be performed in a manner in which HMD can be recovered substantially free of THA.

U.S. Pat. No. 6,300,497 B1 teaches a method for reducing the THA content of a THA/HMD mixture by distillation using column head pressures between 0.3 and 3.0 bar, as well as reducing the THA content of a THA/ACN mixture by distillation using column head pressures between 0.1 and 1.3 bar. U.S. Patent Application No. 2003 0023083 teaches a method for reducing the THA content of a THA/HMD mixture by distillation using column head pressures between 0.001 and 0.3 bar, as well as reducing the THA content of a THA/ACN mixture by distillation using column head pressures between 0.001 and 0.2 bar. However, neither of these disclosures teaches a method in which a three component ACN/HMD/THA mixture is distilled so that the ACN and the HMD can be separated from one another in such a way that a substantial portion of the THA remains with the ACN, particularly when the three component ACN/HMD/THA mixture is one that is derived from the product that is produced by the partial hydrogenation of ADN, such a product containing unreacted ADN that is capable of being isomerized into undesirable CPI if distillation temperatures in the refining train exceed about 195 degrees C.

U.S. patent application Ser. No. 10/383,947 discloses a method for recovering HMD and ACN from a mixture comprising HMD, ACN, THA, and ADN, the method comprising the steps (a) and (b) below:

(a) introducing a mixture comprising HMD, ACN, THA, and ADN into a first distillation column; separating as a group the HMD, ACN and at least a portion of the THA from the ADN, while minimizing isomerization of the ADN into CPI; and then (b) introducing the stream of HMD, ACN and the THA into a second distillation column and separating a distillate comprising HMD from column tails comprising ACN under conditions so that the THA separates along with the ACN in the tails.

Step (b) is accomplished preferably under column conditions of head pressure of at least about 200 mm Hg absolute and a pressure drop across the column of greater than about 25 mm Hg. Under these column conditions, however, there is significant formation of dimers of ACN and HMD as well as mixed dimers of ACN and HMD that separate along with the ACN and the THA in the column tails. Presence of these dimers in the ACN and THA is believed to be detrimental to catalyst life in the process of making caprolactam from the column tails.

It would, therefore, be desirable to have a method of producing a mixture comprising ACN and THA that is substantially free of dimers of ACN and HMD as well as mixed dimers of ACN and HMD for use in making caprolactam without greatly affecting catalyst life. The present invention provides such a method.

SUMMARY OF THE INVENTION

The present invention provides a method of separating a feed mixture comprising ACN and HMD, comprising:
  introducing a feed mixture comprising ACN, THA, and HMD into a refined distillation column; and
  operating the refined distillation column under conditions such that:
    a refined column distillate comprising HMD is withdrawn from the refined distillation column;
    a refined column side draw comprising ACN, THA and low levels of dimers of ACN and HMD is withdrawn from the refined distillation column; and
    a refined column tails comprising ACN, THA and high levels of dimers of ACN and HMD is withdrawn from the refined distillation column,
    a refined column tails comprising ACN, THA and high levels of dimmers of ACN and HMD is withdrawn from the refined distillation column,
  wherein the level of dimers of ACN and HMD in the refined column tails substantially exceeds the level of dimers of ACN and HMD in the refined column side draw.

The refined column distillate comprising HMD is suitable for use in the production of Nylon-6,6. The refined column side draw comprising ACN, THA and relatively low levels of dimers of ACN and HMD is suitable for use in the manufacture of caprolactam without greatly affecting catalyst life, which caprolactam can in turn be used in the production of Nylon-6.

Further provided is a method for increasing the recovery of ACN from a feed stream comprising HMD, ACN, THA and low boilers (LB), wherein the tails of the refined distillation column previously described is further distilled such that the resulting distillate, which comprises primarily ACN and THA, can be reintroduced into the refined distillation column, increasing the recovery of ACN from the feed stream of HMD, ACN, THA and low boilers (LB).

A suitable feed stream for the refined distillate column can be prepared from the distillate produced by vacuum distillation of a mixture comprising an ammonia-depleted mixture of HMD, ACN, THA, ADN, LB and high boilers (HB).

DETAILED DESCRIPTION OF DRAWING

The drawing consists of one FIGURE (FIG. 1) suitable for operating the processes of the present invention.

DETAILED DESCRIPTION OF THE INVENTION

Referring now to FIG. 1, there is shown an apparatus 10 suitable for operating the processes of the present invention. A feed mixture 12 comprising HMD, ACN, THA and other low boilers (LB) is introduced into a refined distillation column 14. The head pressure should be in the range of about 200 to 760 mm Hg absolute. A preferred head pressure is about 400 mm Hg absolute. The column should be operated with a reflux ratio in the range of about 1 to 10. The column pressure drop should be in the range of about 25 to 300 mm Hg. Under these conditions HMD, LB and at most 10 wt % of total THA in the feed are removed as a refined column distillate 16 from the top of the refined distillation column 14. The refined column distillate 16 preferably contains less than about 100 ppm THA. Operation of the refined distillation column 14 above about 200 mm Hg allows the majority of the THA to be preferentially removed in the refined column tails 18 along with ACN. If the head pressure is less than about 200 mm Hg, progressively more THA partitions into the refined column distillate 16.

Under the above operating conditions of the refined distillation column 14, dimers of ACN and HMD are known to form, and chemical analysis shows that a majority of the dimers thus formed remain with the refined column tails 18, which further comprises ACN and THA. Under the above operating conditions, the refined column tails 18 contains less than about 1 wt % dimers. Less dimer formation may be observed at lower temperature and lower pressure operation, but the partitioning of THA is unfavorable at these conditions.

Dimers amounting to less than 50% of the total dimer generation in the refined distillation column are found in the refined column side draw 20, which further comprises ACN and THA. Reduced dimer content in the refined column side draw ACN and THA mixture is desirable for catalyst life during caprolactam production. The level of dimers in the refined column side draw 20 is sufficiently low that it is suitable for use in the production of caprolactam, without greatly affecting catalyst life.

The refined column tails 18 can further be distilled in a recycle distillation column 22. The head pressure in the recycle distillation column 22 should be maintained below about 50 mm Hg absolute, preferably about 20 mm Hg absolute. Under these conditions, a recycle column distillate 24 comprising substantially ACN and THA separates from a recycle column tails 26 comprising substantially dimers. All or a part of the recycle column distillate 24 can then be either re-introduced into the refined distillation column 14, thus increasing the recovery of ACN from the original feed stream 12, or combined with refined column side draw 20.

The feed mixture 12 to the refined distillation column 14 can be produced by distillation of an ammonia-depleted crude feed mixture 28 comprising HMD, ACN, THA, ADN, LB and other high boilers (HB) in a crude distillation column 30. The feed mixture typically contains about 1–90 wt % ADN, 1–90 wt % ACN, 1–90 wt % HMD, <1 wt % THA, <2 wt % LB and <2 wt % HB. In crude distillation column 30, HMD, ACN, THA and LB are removed as crude column distillate 32 and ADN, HB and minor portions of the ACN, HMD and THA are removed as crude column tails 34. Crude distillation column 30 is preferably a vacuum distillation column that contains structured packing. The crude distillation column 30 operates at about 5 to 100 mm Hg absolute, preferably at about 60 mm Hg absolute head pressure, with a reflux ratio of about 1.0. Operation of the crude distillation column 30 at about 60 mm Hg absolute head pressure avoids the need for a column having an excessively large diameter. The withdrawal rate of crude column tails 34 should be adjusted to maintain a temperature below about 195 degrees C. Maintenance of the crude column tails temperature below about 195 degrees C. reduces isomerization of the ADN into CPI. CPI is undesirable since it can form AMCPA when the recovered ADN is hydrogenated, and AMCPA adversely affects the quality of Nylon 6, 6 made from HMD. Crude column distillate 32 can be used as feed mixture 12 for the refined distillation column 14.

Crude column tails 34 can be further distilled in a tails distillation column 36 in which ACN, THA and a minor portion of HMD are removed as tails column distillate 38 and the major portion of ADN, CPI and HB, are removed as tails column tails 40. Tails distillation column 36 is preferably a vacuum distillation column containing structured packing and operating at a head pressure of about 10 to 60 mm Hg absolute, preferably about 20 mm Hg absolute, with a reflux ratio of about 1.0. All or a portion of the tails column distillate 38 can be reintroduced into the crude distillation column 30. Operation of the crude distillation column at a head pressure of about 20 mm Hg absolute allows efficient separation of ACN from ADN without causing an undesirable high temperature of the tails column tails 40, which can result in the formation of CPI The ammonia-depleted crude feed mixture 28 can be made from a crude feed mixture comprising HMD, ACN, THA, ADN, LB, HB and ammonia by processing in an ammonia flasher (not shown). The ammonia flasher generally operates at atmospheric pressure and a person skilled in the art can determine the operating conditions of a flasher given the feed composition.

EXAMPLES

The examples below illustrate the invention as claimed herein and are not intended to be limiting.

Comparative Example

A mixture containing 56 wt % HMD, 43 wt % ACN, approx 2300 ppm THA, <2 wt % LB and no detectable dimer was continuously distilled to separate the HMD as column distillate from the ACN as column tails. The column head pressure was 400 mm Hg and there was 10 feet of Koch/Glitch BX packing below the feed point, i.e. down to the bottom of the column. The same packing was used for the 10 feet zone above the feed point. A reflux ratio of about 1.0 was used in the column operation. The column was controlled to obtain less than 0.1 wt % HMD in the tails. Under these conditions the ACN product (column tails) contained 0.47 wt % dimer due to dimer generation in the column, and the reboiler temperature was 210 degrees C. In addition to the above components, the column tails contained 3 to 4 wt % THA.

Example 1

A mixture containing 58 wt % HMD, 39 wt % ACN, 1.75 wt % THA, <2 wt % LB and no detectable dimer was continuously distilled to separate the HMD as column distillate from the ACN as column tails. The column head pressure was 400 mm Hg absolute and there was 10 feet of Koch/Glitch BX packing below the feed point, at which point the side draw was located. Below the side draw point there was an additional 3 feet of the same packing, i.e. down to the bottom of the column. The same packing was used for the 10 feet zone above the feed point. A reflux ratio of about 1.0 was used in the column operation. The column was controlled to obtain less than 0.1 wt % HMD in the bottoms. Under these conditions the ACN side draw product contained 0.15 wt % dimer and about 3 to 4 wt % THA. The tails stream draw was adjusted to control the tails temperature between 220 and 225 degrees C. Under these conditions the tails stream contained 71 wt % ACN, 4.8 wt % THA and 13 wt % dimer. The column was operated at a reflux ratio of about 1.0.

The tails stream was then batch distilled at a head pressure of about 20 mm Hg absolute in a column having 5 feet of BX packing using a reflux ratio of about 2.5. The ACN was distilled overhead until the reboiler temperature reached 225 degrees C. The amount of ACN recovered as distillate was >98% of the initial charge of the batch column, and there was no detectable dimer in the distillate. The distillate contained 93 wt % ACN and 7 wt % THA.

It is to be understood that the embodiments and variations shown and described herein are merely illustrative of the principles of this invention and that various modifications may be implemented by those skilled in the art without departing from the scope and spirit of the invention.

What is claimed is:

1. A method of separating a feed mixture comprising 6-aminocapronitrile (ACN) and hexamethylenediamine (HMD), comprising:
   introducing a feed mixture comprising ACN, tetrahydroazepine (THA) and HMD into a refined distillation column; and
   operating the refined distillation column under conditions such that:
     a refined column distillate comprising HMD is withdrawn from the refined distillation column;
     a refined column side draw comprising ACN, THA and low levels of dimers of ACN and HMD is withdrawn from the refined distillation column; and
     a refined column tails comprising ACN, THA and high levels of dimers of ACN and HMD is withdrawn from the refined distillation column,
   wherein the levels of dimers of ACN and HMD in the refined column tails substantially exceeds the level of dimers of ACN and HMD in the refined column side draw.

2. The method of claim 1 wherein the head pressure of the refined distillation column is about 200 to about 760 mm Hg absolute and the pressure drop across the refined distillation column height is about 25 to about 300 mm Hg.

3. The method of claim 2 wherein the head pressure of the refined distillation column is about 200 mm Hg absolute and the pressure drop across the refined distillation column height is greater than about 25 mm Hg.

4. The method of claim 1 further comprising:
   introducing the refined column tails into a recycle distillation column; operating the recycle distillation column under conditions such that:
     a recycle column distillate comprising ACN and THA is withdrawn from the recycle distillation column;
     a recycle column tails comprising dimers of ACN and HMD is withdrawn from the recycle distillation column; and
   introducing at least some of the recycle column distillate into the refined distillation column along with the feed mixture.

5. The method of claim 4 wherein the head pressure of the recycle distillation column is less than about 50 mm Hg absolute.

6. The method of claim 5 wherein the head pressure of the recycle distillation column is less than about 20 mm Hg absolute.

7. The method of claim 1 further comprising;
   introducing an ammonia-depleted crude feed mixture comprising HMD, ACN, THA and adiponitrile (ADN) into a crude distillation column; and
   operating the crude distillation column under conditions to minimize isomerization of ADN into 2-cyanocyclopentylideneimine (CPI) such that:
     a crude column distillate comprising HMD, ACN and THA is withdrawn from the crude distillation column; and
     a crude column tails comprising ADN, HMD, ACN and THA is withdrawn from the crude distillation column;
   wherein the crude column distillate comprises the feed mixture for the refined distillation column.

8. The method of claim 7 wherein the head pressure of the crude distillation column is about 5 to about 100 mm Hg absolute.

9. The method of claim 8 wherein the head pressure of the crude distillation column is about 60 mm Hg absolute.

10. The method of claim 7 further comprising:
    introducing the crude column tails into a tails distillation column; operating the tails distillation column under conditions such that:
      a tails column distillate comprising HMD, ACN and THA is withdrawn from the tails distillation column; and
      a tails column tails comprising ADN and CPI is withdrawn from the tails distillation column; and
    reintroducing the tails column distillate into the crude distillation column.

11. The method of claim 10 wherein the head pressure of the tails distillation column is about 10 to about 60 mm Hg absolute.

12. The method of claim 11 wherein the head pressure of the tails distillation column is about 20 mm Hg absolute.

* * * * *